US008742903B2

(12) United States Patent
Cobb

(10) Patent No.: US 8,742,903 B2
(45) Date of Patent: Jun. 3, 2014

(54) GENEDRIVE RFID

(75) Inventor: Ben Cobb, Wiltshire (GB)

(73) Assignee: Epistem Limited, Manchester (GB)

( * ) Notice: Subject to any disclaimer, the term of this patent is extended or adjusted under 35 U.S.C. 154(b) by 149 days.

(21) Appl. No.: 13/345,115

(22) Filed: Jan. 6, 2012

(65) Prior Publication Data
US 2012/0200396 A1 Aug. 9, 2012

(30) Foreign Application Priority Data

Jan. 6, 2011 (GB) .................................. 1100152.6

(51) Int. Cl.
H04Q 5/22 (2006.01)
(52) U.S. Cl.
USPC .... 340/10.5; 340/10.6; 340/10.51; 340/10.52
(58) Field of Classification Search
USPC ....................... 340/10.1–10.52, 572.1–572.9;
422/68.1, 69–72, 119, 159, 400–429;
435/3, 286.1–305.4; 700/266–274
See application file for complete search history.

(56) References Cited

U.S. PATENT DOCUMENTS

| 6,165,778 | A | * | 12/2000 | Kedar | ............................. 506/33 |
| 2004/0136879 | A1 | * | 7/2004 | Meier et al. | .................... 422/109 |
| 2005/0079109 | A1 | * | 4/2005 | Meier | ........................... 422/130 |
| 2006/0199196 | A1 | | 9/2006 | O'Banion et al. | |
| 2008/0233012 | A1 | * | 9/2008 | Zander | ............................ 422/99 |
| 2008/0238627 | A1 | * | 10/2008 | Oldham et al. | ............. 340/10.1 |
| 2008/0284602 | A1 | * | 11/2008 | Morris et al. | ............. 340/572.1 |
| 2009/0032592 | A1 | * | 2/2009 | Christensen | .................. 235/439 |
| 2009/0047713 | A1 | | 2/2009 | Handique | |
| 2009/0129978 | A1 | | 5/2009 | Wilson et al. | |
| 2009/0317874 | A1 | | 12/2009 | Dale et al. | |
| 2010/0001854 | A1 | * | 1/2010 | Kojima | ......................... 340/500 |
| 2010/0007501 | A1 | * | 1/2010 | Yang et al. | ................. 340/572.8 |
| 2010/0015614 | A1 | | 1/2010 | Beer et al. | |
| 2010/0054997 | A1 | * | 3/2010 | Ooe | .............................. 422/68.1 |
| 2010/0110439 | A1 | * | 5/2010 | Gruler et al. | ................... 356/440 |
| 2010/0112683 | A2 | * | 5/2010 | Atwood et al. | ............. 435/303.1 |
| 2010/0173393 | A1 | * | 7/2010 | Handique et al. | .......... 435/287.2 |
| 2010/0190152 | A1 | * | 7/2010 | Squirrell | ........................... 435/6 |
| 2010/0227383 | A1 | * | 9/2010 | Amano et al. | ............. 435/287.2 |
| 2010/0297640 | A1 | * | 11/2010 | Kumar et al. | ..................... 435/6 |

(Continued)

FOREIGN PATENT DOCUMENTS

GB 2455204 6/2009
WO WO 97/21090 A1 * 6/1997 ............. G01N 21/07

OTHER PUBLICATIONS

UK Search Report for GB1100152.6 dated Apr. 8, 2011.

Primary Examiner — Hai Phan
Assistant Examiner — Orlando Bousono
(74) Attorney, Agent, or Firm — Choate, Hall & Stewart LLP; Brenda Herschbach Jarrell

(57) ABSTRACT

The present invention provides a method of operating a thermal cycler using readable tags (for example, Radio Frequency Identification (RFID)) to simplify the operation and to reduce user interaction requirements. The RFID tag is used to program the thermal cycler unit. This automates process flow and allows single button operation. In general terms, the invention uses RFID tags provided on reaction vessels to identify a particular vessel; while a readable program card contains data associating reaction vessel identities with specific operations (eg, thermal cycling program, detection steps) to be performed on that vessel. The thermal cycler detects the reaction vessel RFID tag, and selects an appropriate operation to perform.

35 Claims, 8 Drawing Sheets

(56) References Cited

U.S. PATENT DOCUMENTS

2011/0045565 A1* 2/2011 Sanders et al. ............. 435/173.1
2011/0084842 A1* 4/2011 Tzidon et al. ................. 340/603
2012/0041111 A1* 2/2012 Christensen et al. ......... 524/111

* cited by examiner

GENEDRIVE RFID

CROSS-REFERENCE TO RELATED APPLICATIONS

The present application claimed priority to Great Britain Application No. 110,152.6, filed Jan. 6 2001, the entire contents of which is incorporated herein by reference.

FIELD OF THE INVENTION

The present invention relates to a method for operating a thermal cycler, and to a method of associating particular reaction vessels with particular cycling programs and/or with particular tests to be carried out. Aspects of the invention relate to kits for use in such methods.

BACKGROUND

Many diagnostic tests rely on the use of thermal cyclers to carry out a PCR (polymerase chain reaction) type amplification of nucleic acids. PCR allows specific nucleotide sequences to be amplified in a sample, thereby allowing detection of sequences which may otherwise be present in the sample at very low levels. Sequences may be detected for example by use of labelled probes, or by determining thermal hybridisation profiles. However, the cycling steps and the detection steps tend to be sequence- or test-specific. It is necessary therefore either to have a cycler which is freely programmable, leading to increased complexity of operation and greater potential for user error, or which has a restricted set of permissible operations, leading to limited flexibility and problems in extending operation to different tests.

This constraint is particularly difficult in PCR applications because the program and result is multifactorial, the thermal profile may be different for each test, and the results will differ from target to target.

It is among the objects of the present invention to provide an alternative method for operating a thermal cycler which reduces or avoids these disadvantages.

Certain aspects of the present invention integrate the programming and reporting of diagnostic assays through RFID and create a full auditing trail for future reference. It enables different assays to be run on the same platform without the need to store all possible tests or for the user to 'program' the test parameters which would complicate the system. In preferred embodiments, operation is via a single button process.

SUMMARY

The present invention provides a method of operating a thermal cycler using readable tags (for example, Radio Frequency Identification (RFID)) to simplify the operation and to reduce user interaction requirements. The RFID tag is used to program the thermal cycler unit. This automates process flow and allows single button operation, which in turn reduces chances for human error. The method also provides flexibility since future assays may be developed independent of platform firmware updates. Aspects of the invention also allow integration of all critical information and archiving of results, and optionally permit integration of operator details e.g. for chain of custody and patient auditing.

In general terms, the invention uses RFID tags provided on reaction vessels to identify a particular vessel; while a readable program card contains data associating reaction vessel identities with specific operations (eg, thermal cycling program, detection steps) to be performed on that vessel. The thermal cycler detects the reaction vessel RFID tag, and selects an appropriate operation to perform.

According to a first aspect of the present invention, there is provided a system comprising:
a) a reaction vessel including an identification tag readable by a remote reader and including data identifying the reaction vessel;
b) a computer readable medium including data representing one or more reaction vessel identities and associated processing information; and
c) a thermal cycler including a remote reader for reading the vessel identification tag, and means for reading the computer readable medium.

A further aspect of the invention provides a kit for use with a thermal cycler including a remote reader and means for reading a computer readable medium, the kit comprising:
a) a reaction vessel including an identification tag readable by a remote reader and including data identifying the reaction vessel; and
b) a computer readable medium including data representing one or more reaction vessel identities and associated processing information.

A still further aspect of the present invention provides a method of operating a thermal cycler including a remote reader and means for reading a computer readable medium, the method comprising:
a) providing a reaction vessel including an identification tag readable by a remote reader and including data identifying the reaction vessel; and a computer readable medium including data representing one or more reaction vessel identities and associated processing information;
b) allowing the cycler to read the computer readable medium to determine said one or more reaction vessel identities and associated processing information;
c) allowing the cycler to read the vessel identification tag, to determine the identity of the vessel;
d) allowing the cycler to compare the identity of the vessel with the reaction vessel identities obtained from the computer readable medium, and to select an appropriate process to perform associated with the particular vessel;
e) allowing the cycler to perform the selected process on the reaction vessel; and
f) allowing the cycler to display the results of said performed process.

A yet further aspect of the present invention provides a method of performing a diagnostic test using a reaction vessel having an identification tag readable by a remote reader; and a thermal cycler including a remote reader and means for reading a computer readable medium, the method comprising:
a) reading a readable tag from the reaction vessel, to determine the identity of the vessel;
b) comparing the identity of the vessel with stored data obtained from the computer readable medium representing one or more reaction vessel identities and associated processing steps of a diagnostic test;
c) selecting an appropriate processing step associated with the reaction vessel identity to perform;
d) performing the selected processing step on the reaction vessel; and
e) displaying the result of the performed processing step.

The following comments apply to all aspects of the invention, unless otherwise stated. Preferably the identification tag is a radio tag, more preferably an RFID tag. The tag may include data representing the identity of the vessel, for example, as a numerical identifier. Embodiments of the invention may include a plurality of reaction vessels, each having an identification tag; in which case the identity of the vessel is preferably unique. In certain embodiments of the invention, the identification tag may also be writable by the thermal cycler. Thus, the methods of the invention may further comprise the step of writing to the tag after performing the selected processing step to identify the reaction vessel as used. The step of reading the tag in such methods may also comprise the step of confirming that the reaction vessel has not previously been used prior to proceeding with the method.

Alternatively, or in addition, methods of the invention may further comprise the step of writing data to the computer readable medium to identify a particular reaction vessel identity as having been used. The step of comparing the identity of the vessel with the reaction vessel identities may further include the step of confirming that the reaction vessel has not previously been used prior to proceeding with the method.

The step of reading the reaction vessel tag may be carried out after the vessel has been loaded into the cycler, but preferably is carried out remotely, before the vessel has been loaded into the cycler. Remote reading simplifies operation as the processing step may be selected and readied before the user needs to load the vessel.

The processing information stored on the computer readable medium may represent a thermal cycling reaction; for example, a PCR amplification program. The information may also include data relating to detection of results from the cycling reaction; for example, thermal profile of amplification products, detection of amplified products using suitable probes, and the like. The information may further comprise expected results for a particular reaction, and/or tolerances for these expected results. The computer readable medium may further comprise data representing the manufacturing and/or expiry dates of the particular reaction vessel or kit, lot number, batch number, and any other suitable identification data. The methods of the invention may further comprise the step of verifying any of this data, for example, the expiry date, prior to proceeding with the method.

The computer readable medium may also be a writable medium. The methods may further comprise the step of writing data representing the results of the performed process step to the medium. The written data is preferably associated with the relevant reaction vessel identity. This provides a record of the performed tests; the computer readable medium may be stored and/or archived to provide a permanent record or a backup record.

In certain embodiments, the computer readable medium may be read and/or written remotely, for example using RFID, Bluetooth or WiFi technology, without the need to physically load the medium into the cycler.

Displaying the results of the performed process may comprise displaying said results on a display screen; and/or may comprise generating a printed copy of the results.

The methods may also comprise the step of storing read data from the computer readable medium in a local memory. The data may be retained in local memory even in the absence of the computer readable medium; in this way the cycler may be programmed once with a particular protocol for a test kit and then used when necessary. In alternative embodiments of the invention, however, the method may comprise confirming the presence of the computer readable medium prior to operating the cycler, such that diagnostic tests cannot be performed in the absence of the computer readable medium.

The system, the kit, and/or the reaction vessel may further comprise any or all of the reagents necessary for conducting a diagnostic assay on a sample. For example, the kit may be provided together with reaction buffers, primers, nucleotides, and enzymes, for carrying out a PCR amplification.

The reaction vessel may further comprise a label including visual indicia identifying the reaction vessel. The indicia may include at least some of the same information as is included in the RFID tag, and/or in the computer readable medium. For example, the label may include a written representation of the vessel identity, and may include details such as the lot and batch number of the vessel, or the name of the diagnostic test to be conducted. The label may include a removable portion; preferably this includes at least a written representation of the vessel identity. In preferred embodiments the written representation of the vessel identity is duplicated, being present both on the removable portion and on the other portion of the label. This allows the removable portion to be removed and archived while still retaining the same information on the vessel itself. The removable portion of the label may further include an area on which a user may write further details; for example, the patient name. The removable portion may be located on top of a non-removable portion of the label, with any written details being duplicated onto the non-removable portion.

The cycler may comprise a single-button user interface; this presents the user with a single button to press in order to operate the device. It will be understood that reference here to a "button" need not mean a physical button, but may include software implementations, for example a touch screen interface or the like. The cycler will include appropriate software or hardware to alter the function of the button depending on the stage of operation reached in the methods. For example, in certain embodiments of the invention, the methods include the step of pausing operation of the cycler after certain steps of the methods, and awaiting user confirmation to proceed by pressing the button. The methods may further comprise the step of displaying an appropriate message on a screen of the cycler—which may be the same as the touch screen interface where this is used—informing the user of the next step to be taken.

For example, in an inactive or sleep mode, the screen may display the message "touch here to begin"; when a user touches the screen, the cycler will activate and will move to the first step in the method. Another example may be after the processing step has been selected, the cycler may display the message "touch here to begin diagnostic test", or may include the name of the diagnostic test. Once processing has finished, the screen may display the message "touch here to view results".

This method allows for a simple, controlled operation of process flow, such that a user may proceed stepwise through the diagnostic test by means of a simple interface. This reduces the risk of user error, while still allowing great flexibility in terms of possible diagnostic tests to be performed.

The methods may further comprise the step of detecting a button press of longer than a predetermined duration, and pausing operation on detecting such a press. This allows the user to pause operation if desired. Alternatively, or in addition, the methods may comprise detecting a button press of longer than a further predetermined duration, and resetting the cycler on detecting such a press. The two may be combined; for example, a first long button press may pause operation, with a second long press being required to reset the cycler. A message to this effect may be displayed after the first long button press. In certain embodiments of the invention, a short press after the long press may be used to unpause operation.

The methods may further comprise the step of detecting the presence of a user identification code prior to operating the cycler. For example, the user identification code may be stored on a separate computer readable medium which must be loaded onto the cycler prior to operation. Alternatively, an RFID tag may be used containing a user identifier. The detected code may be compared with a list of authorised user codes. Where the results of the process are written to computer readable medium, the results may be associated with the detected user code. These steps allow for more control over authorisation of users, and may be useful in forensic methods and the like, where audit trails and traceability are important.

BRIEF DESCRIPTION OF THE DRAWING

These and other aspects of the present invention will now be described with reference to the accompanying figures, which show.

DETAILED DESCRIPTION OF CERTAIN EMBODIMENTS

Aspects of the present invention provide a method of operating a thermal cycler which allows for flexibility in the type of diagnostics to be carried out, while presenting a constrained process flow and simplified user interface to reduce the risks of user error and simplify operation. In certain embodiments this is achieved through a combination of use of RFID tags to identify reaction vessels, program cards to program the cycler with appropriate cycling reactions, and a single button user interface. The method is particularly intended for carrying out diagnostic tests on patient samples for healthcare or forensic purposes.

The method uses a thermal cycler which includes an RFID reader, and an interface for receiving computer readable media (for example, an SD card or a USB memory stick). The cycler is also able to write to the media. The cycler further includes a display screen having a touch sensitive panel for user interaction.

Figure 3:
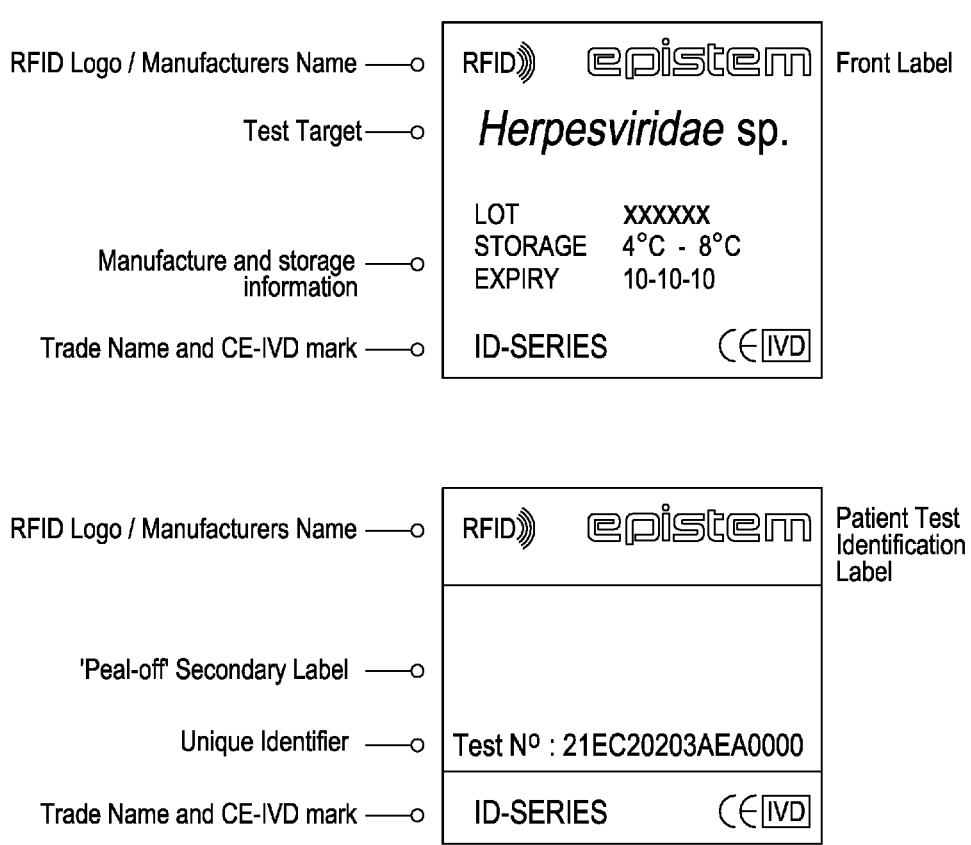
FIGS. 3 and 4 show labels for use with reaction vessels.
Figure 4:
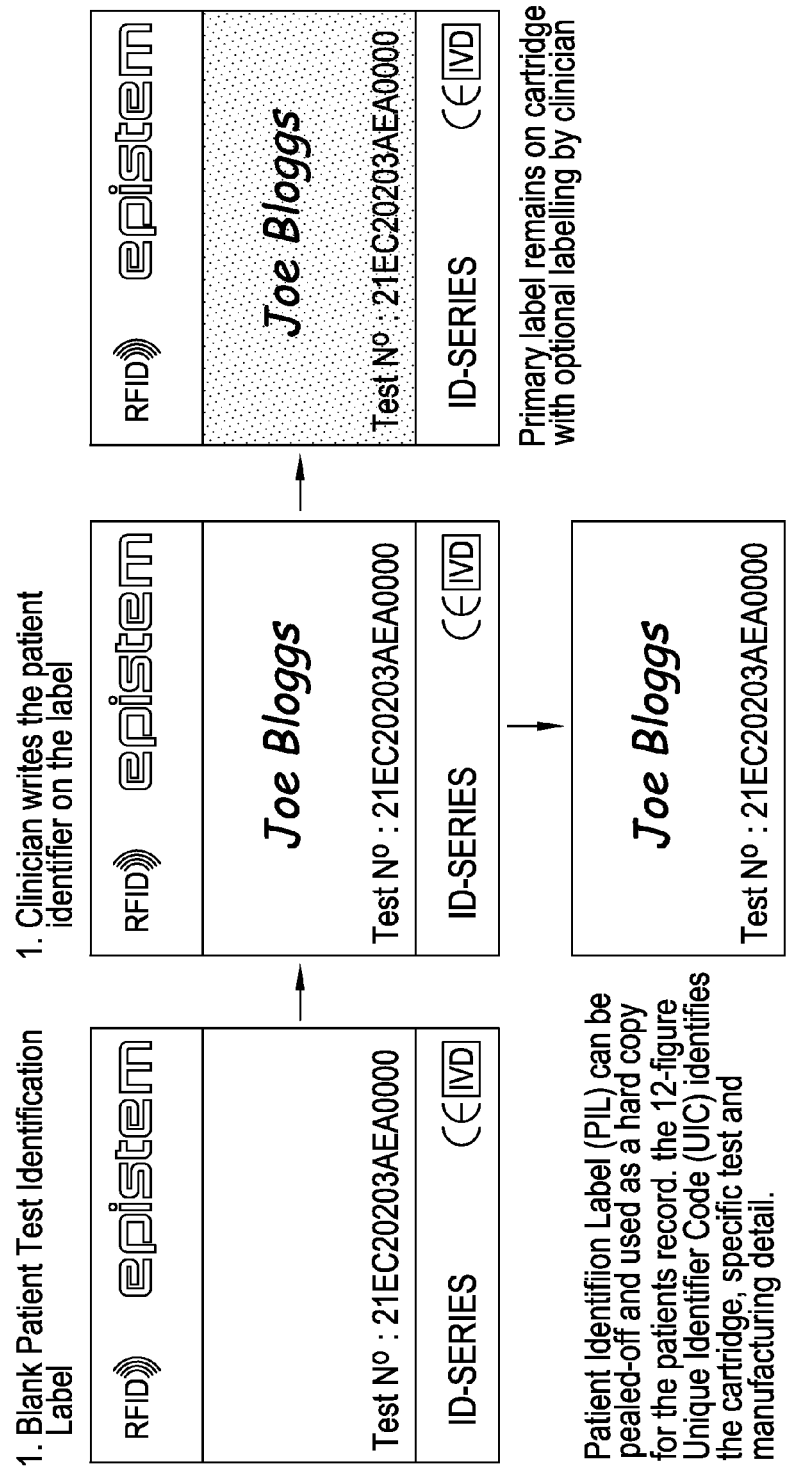

A diagnostic test kit includes a set of reaction vessels, each of which may be pre-loaded with the necessary reagents (PCR primers, buffers, enzymes, etc) for carrying out a particular diagnostic test, such as detection of a particular DNA sequence in a patient sample. The kit also includes instructions for use. Each reaction vessel carries a label having an RFID chip on which is recorded a unique identifying number for that particular vessel. The labels are also printed with the identifying number, as well as details of the diagnostic test, and manufacture and storage information. A sample label is shown in FIG. 3. An alternative label is shown in FIG. 4; this includes a removable section (patient information label, PIL) on which a clinician may write patient details before removal; the PIL may then be retained in the patient's record as a hard copy of the test.

Information written on the removable section is also transferred to the permanent section of the label underlying this by means of a suitable coating.

Also included in the diagnostic test kit is a program card, in the form of an SD card or USB memory stick or the like. The program card includes data representing each of the reaction vessel identifying numbers, together with the associated diagnostic test (for example, thermal cycler times, expected results, tolerance limits etc). The card may also include data representing manufacture, storage, and expiry information for the test kit. The kit may include a number of different diagnostic tests; if so, appropriate data will be recorded on the program card for each reaction vessel.

Figure 1:
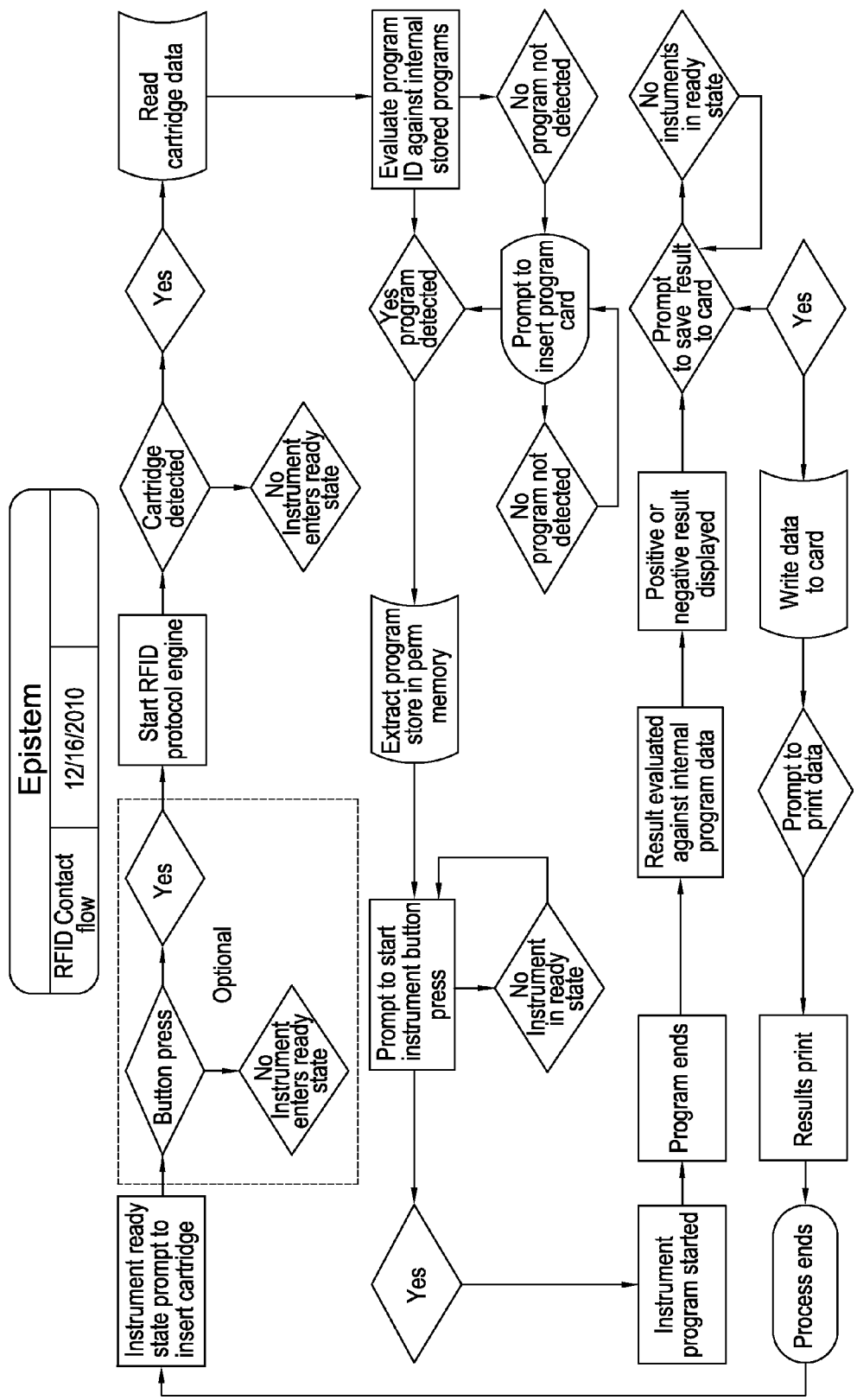
FIG. 1 is a flow diagram representing an example process flow for a method of the present invention.

When a user has a patient sample, it is loaded into the appropriate reaction vessel, and operation of the cycler begins. An illustrative process flow is shown in FIG. 1. This begins at the top left item, "instrument ready state prompt to insert cartridge". That is, the cycler is ready to begin. The screen (shown in FIG. 8a) prompts the user to press the button to register a vessel to the cycler. On button press, the RFID protocol engine is started, and the cycler attempts to detect a reaction vessel via the RFID chip. Detection is preferably remote, that is, without the requirement to load the vessel into the cycler. If the reaction vessel is detected, the data is read from the chip, and the vessel identification number compared against any stored programs in internal memory.

If the identification number is found in a stored program, then the cycler proceeds to the next step. If no identification number is found, then the cycler prompts the user to insert a program card, and to press the button to proceed. When this is done, any program from the card is read to internal memory, and again the vessel identification number compared against the stored program. This is repeated until a program is found which includes the vessel identification number. Then the specific program is extracted (from the card or from stored memory), and the cycler readied to perform that program. The user is prompted to load the reaction vessel (if not already done so), and to press the button to begin the program; details of the program may also be displayed to the user to allow confirmation that the correct program is being used.

Figure 8:
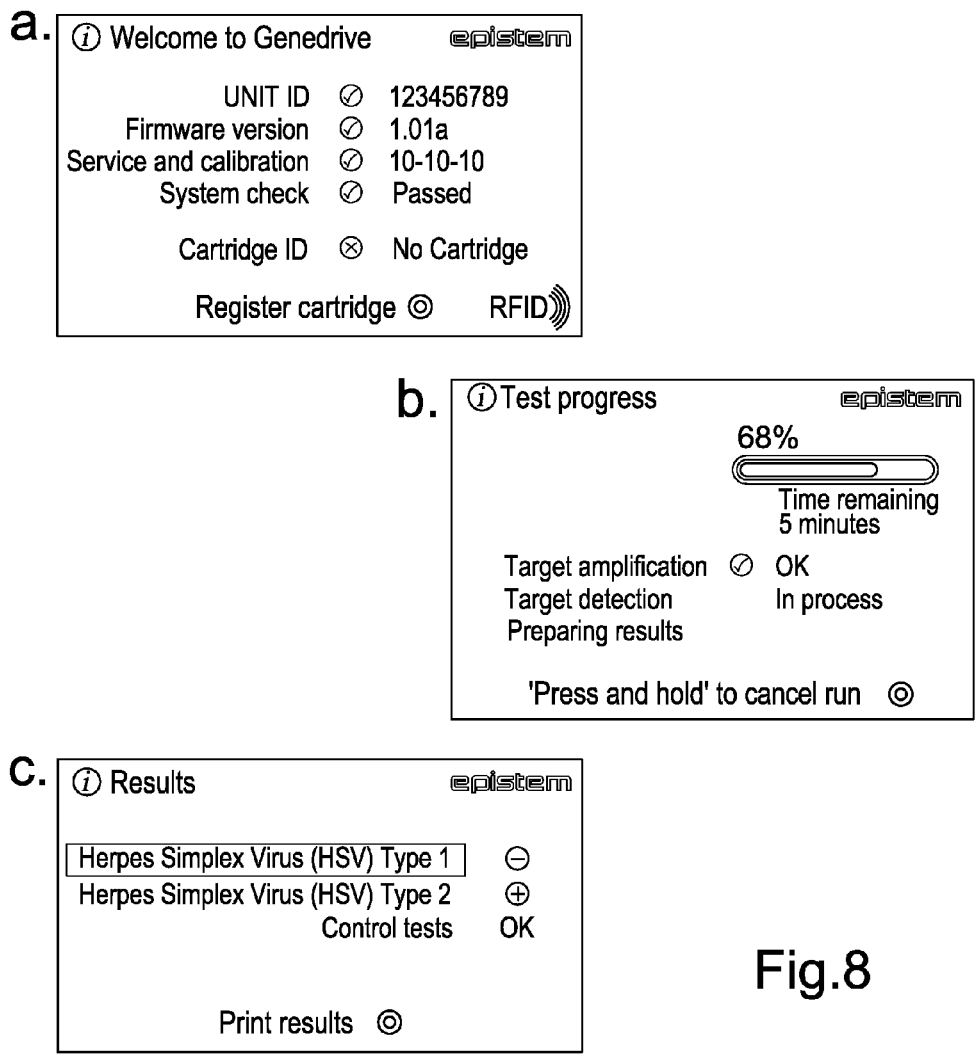
FIGS. 8 and 9 show example user interface displays.

On the button being pressed, the cycler begins operation of the selected program. An "in progress" screen may be displayed during operation, for example as shown in FIG. 8b.

Once the program ends, the result of the operation is evaluated by the cycler against the internal data obtained from the program card (ie, the expected results). A positive or negative result may be displayed (for example, as in FIG. 8c), with the user then being prompted to press the button to save the result to the program card. On the button being pressed, the result of the test is saved to the program card against the particular vessel identification number. This creates a permanent record of the result, and also flags the particular vessel as having been used. In certain embodiments of the invention, the cycler may also write to the RFID chip to indicate that the vessel has been used.

The user is then prompted to print the result, to obtain a hard copy version. Again, this prompt is accompanied by the instruction to press the button. Once this is done, the result is printed, the process ends, and the cycler returns to the ready state with a prompt to insert another reaction vessel.

Note that each of the prompt stages require only a single button press to proceed. If the button is not pressed, the cycler enters a ready state, awaiting a button press to awake. There is also a defined process flow which ensures that all steps of the operation are completed, and which minimises the possibilities for user error. Association of a particular vessel identification number with a particular test also ensures that the correct test is performed on a sample, as well as creating a robust audit trail.

Figure 2:
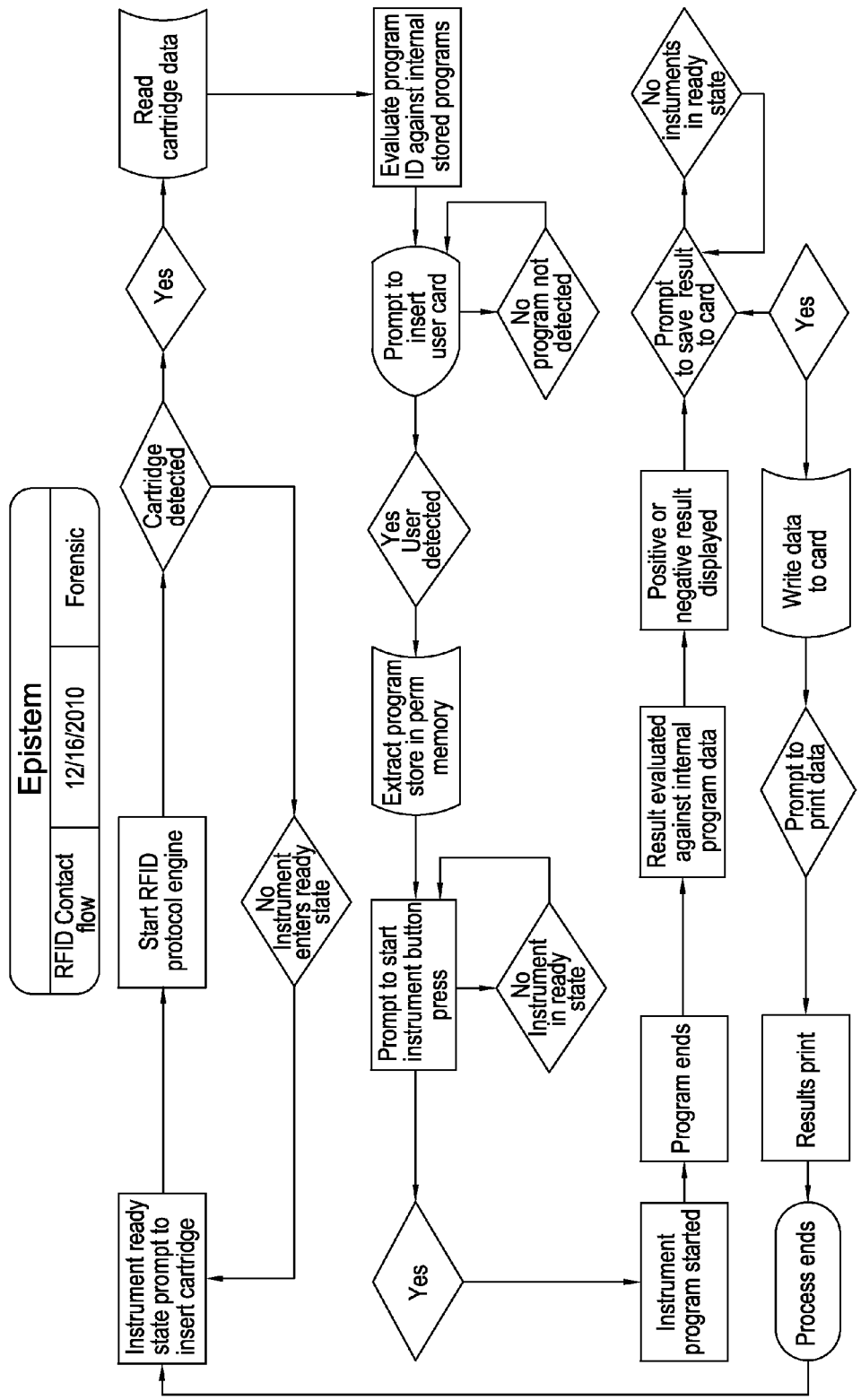
FIG. 2 is an alternative process flow.

A slightly modified process flow is shown in FIG. 2. This is generally similar to that shown in FIG. 1, but includes an additional requirement for a user identification card. The cycler prompts for insertion of this card after identifying the reaction vessel and determining the correct program to use. The user identification card may store a user identity; this is then associated with the vessel identity and stored on the program card to create a record of which user carried out the diagnostic test. Alternatively, or in addition, a list of authorised users may be included on the program card, and the user identity compared with this list before beginning operation.

In summary, the present invention uses Radio Frequency Identification (RFID) to simplify operation and to reduce user interaction requirements. An important aspect of this is single button operation of the cycler, which reduces chances for human error and automates program flow between each stage.

Because of identity protection no patient information is stored apart from the unique RFID identifier which may be linked to the patient independently via the removable portion of the label. Subjective interpretation of results is also avoided, since the program card may include expected results (for example, melt temperatures of hybridized probes); the cycler itself assays the results and reports a simple yes/no result.

Information about production, expiry date are available to audit prior to use so that the cycler can cross reference to determine if the kit is usable. Information about whether the kit has been used is available. This uniquely links entire process; program, results, production data and integrates these with the programming and display of data to the user. Results stored within the cycler data archive, and may be uploaded onto the program card. These may be interrogated by an external reader or device. The program card may be provided with RFID as well, in which case the results from the card may be read by an external device with integrated RFID reader.

Figure 5:
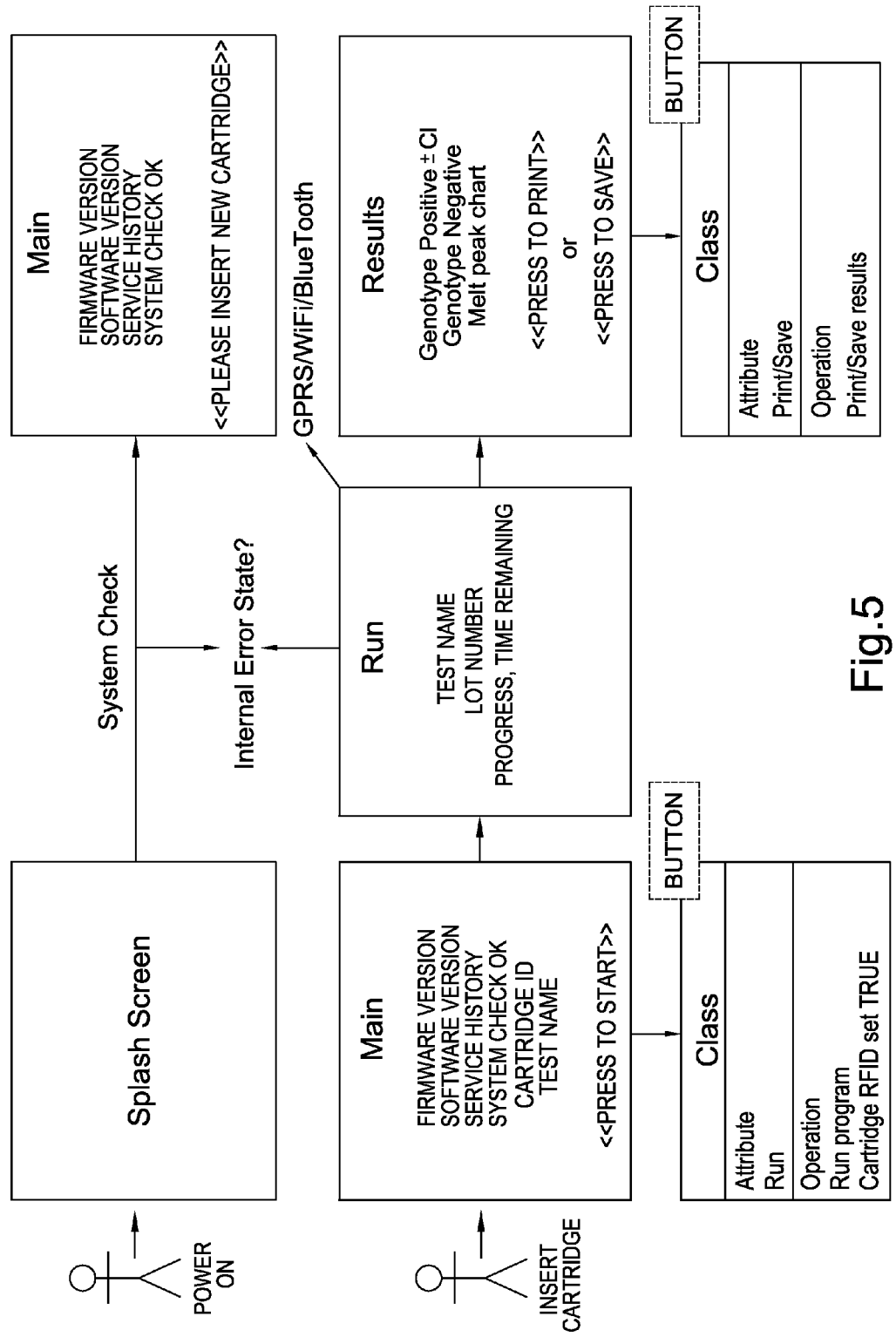
FIGS. 5 to 7 show single button operation diagrams of aspects of the methods of the present invention.
Figure 6:
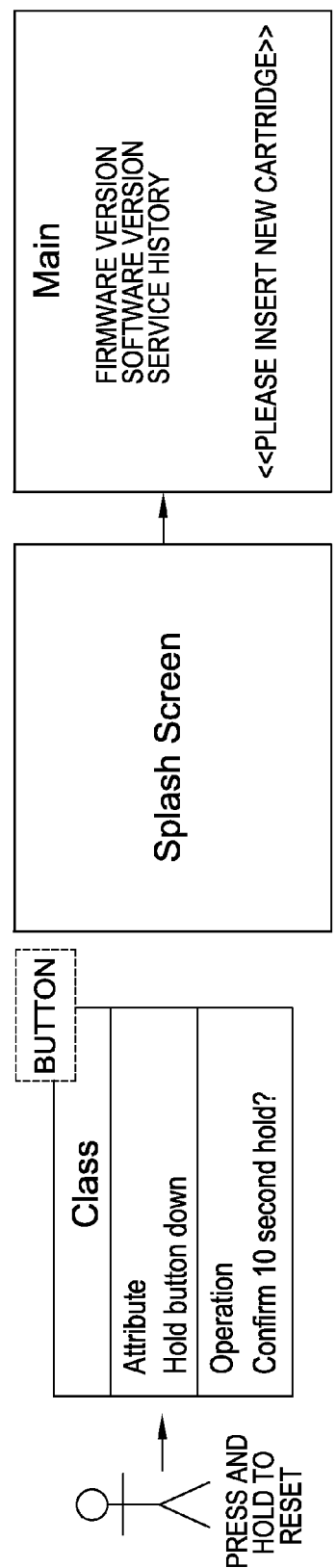
Figure 7:
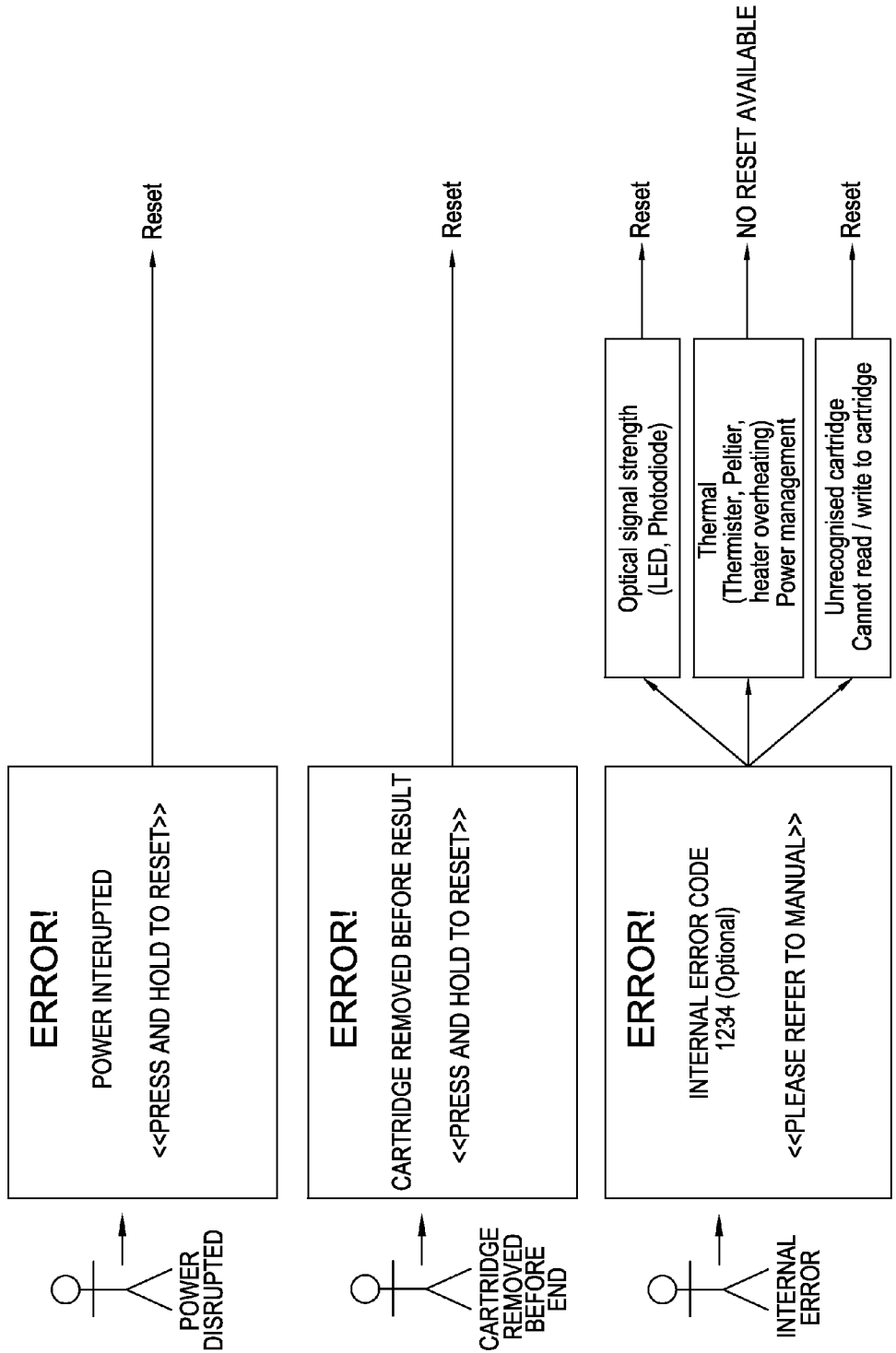
Figure 9:
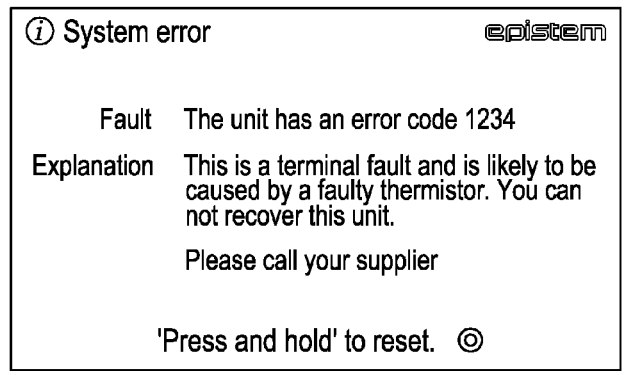

Single button operation is one of the important features of aspects of this invention. Examples of this are shown in FIGS. 5 to 7, which illustrate how the assigned function of the button will alter depending on the stage of the process reached. FIG. 6 shows that a long button press may be used to reset the operation of the cycler at any stage of operation. FIG. 7 shows error checking in the cycler; should an error occur, a reset screen is shown (see FIG. 9 for an example), and the user invited to long press the button to reset. Errors may be recoverable (eg, power interruption, unrecognized vessel), or unrecoverable (eg, hardware failure).

Single button operation with flexibility of programming and ease of use is enabled by use of RFID tags to label reaction vessels and program cards to program the cycler with all necessary information to perform a predetermined diagnostic on a particular vessel. Other aspects of the invention will be apparent from the following claims.

The invention claimed is:

1. A method of performing a diagnostic test using:
   1) a reaction vessel having an identification tag readable by a remote tag reader; and
   2) a thermal cycler including:
      a) the remote tag reader; and
      b) a computer that reads a computer readable medium that contains data associating reaction vessel identities with specific operations to be performed on the reaction vessel; and
      c) a display,
   the method comprising:
   i) providing the reaction vessel in sufficient proximity to the thermal cycler so that the readable identification tag can be read by the remote tag reader; and
   ii) operating the thermal cycler so that it:
      reads the readable identification tag from the reaction vessel so that identity of the reaction vessel is determined;
      queries the computer readable medium with the determined identity so that the associated specific operations for the determined identity are selected;
      performs the selected specific operations on the reaction vessel; and
      displays one or more results of the performed specific operations.

2. The method of claim 1, wherein the readable identification tag is or comprises a radio tag.

3. The method of claim 1, wherein: the thermal cycler further comprises:
   d) means for writing to the readable identification tag; and
   the step of operating the thermal cycler includes operating it so that it writes to the readable identification tag to identify the reaction vessel as used.

4. The method of claim 1, wherein:
   the thermal cycler further comprises:
   d) means for writing to the computer readable medium; and
   the step of operating the thermal cycler includes operating it so that it writes to the computer readable medium and associates the particular reaction vessel identity with a status of having been used.

5. The method of claim 1, wherein:
   the computer readable medium further contains data associating the reaction vessel identities with a status of having or not having been used; and
   the step of operating the thermal cycler includes operating it so that it queries the computer readable medium and determines the status of the reaction vessel as not having been used before it performs the selected operations on the reaction vessel.

6. The method of claim 1, wherein the specific operations associated with at least one reaction vessel identity on the computer readable medium represents a thermal cycling reaction.

7. The method of claim 6, wherein the specific operations associated with at least one reaction vessel identity on the computer readable medium include data relating to any or all of:
   detection of results from the thermal cycling reaction;
   expected results for a particular reaction; and
   tolerances for these expected results.

8. The method of claim 1, wherein the specific operations associated with at least one reaction vessel identity on the computer readable medium further comprises data representing:
   manufacturing and/or expiry dates of the particular reaction vessel or a kit that includes the particular reaction vessel, or
   lot number, or
   batch number, or
   any other suitable identification data.

9. The method of claim 8, wherein the step of operating the thermal cycler further comprises operating it so that it verifies any of the data prior to proceeding with the method.

10. The method of claim 1, wherein:
    the thermal cycler further comprises:
    d) means for writing to the computer readable medium; and the step of operating the thermal cycler includes operating it so that it writes data representing the one or more results of the performed specific operations to the computer readable medium.

11. The method of claim 10, wherein the data is associated with a corresponding reaction vessel identity when written to the computer readable medium.

12. The method of claim 1, wherein the step of displaying the one or more results comprises displaying the one or more results on a display screen; and/or generating a printed copy.

13. The method of claim 1, wherein the step of operating the thermal cycler includes operating it so that it stores read data from the computer readable medium in a local memory.

14. The method of claim 1, wherein the thermal cycler further comprises: a single-button user interface.

15. The method of claim 14, wherein:
the thermal cycler further comprises:
 d) software or hardware, and the step of operating the thermal cycler includes operating it so that it alters the function of the single-button depending on which stage of the specific operations reached is being performed.

16. The method of claim 15, wherein the step of altering function of the single-button comprises:
allowing reactivation of a paused thermal cycler, which has paused after completion of one or more steps of the specific operations and is awaiting user confirmation to proceed.

17. The method of claim 16, wherein the step of displaying the one or more results comprises:
displaying a message on a screen of the display informing the user of one or more steps to be performed for the specific operations.

18. The method of claim 15, wherein the step of altering function of the single-button comprises:
pausing operation or resetting the thermal cycler upon detection of a signal resulting from depressing the single-button for a period of time longer than a predetermined duration.

19. The method of claim 1, wherein step i) further comprises:
detecting a user identification code prior to operating the thermal cycler.

20. The method of claim 19, wherein:
the thermal cycler further comprises:
 d) means for writing to the computer readable medium; and the step of operating the thermal cycler includes operating it so that it writes data representing the one or more results of the performed specific operations to the computer readable medium, such that the data is associated with the detected user identification code when written to the computer readable medium.

21. A system comprising:
a) a reaction vessel including an identification tag readable by a remote tag reader, wherein the identification tag includes data identifying the reaction vessel;
b) a computer readable medium that contains data associating one or more reaction vessel identities with specific operations to be performed on the identified reaction vessel; and
c) a thermal cycler comprising:
 i) the remote tag reader for reading the identification tag of the reaction vessel so that identity of the reaction vessel is determined; and
 ii) a computer for querying the computer readable medium with the determined identity so that the associated specific operations for the determined identity are selected and performed on the identified reaction vessel.

22. The system of claim 21, wherein the identification tag is or comprises a radio tag.

23. The system of claim 21, further comprising a plurality of reaction vessels, each comprising an identification tag.

24. The system of claim 21, wherein the specific operations associated with at least one reaction vessel identity on the computer readable medium represents a thermal cycling reaction.

25. The system of claim 21, wherein the computer readable medium further comprises data representing:
manufacturing and/or expiry dates of the particular reaction vessel or a kit that includes the particular reaction vessel, or
lot number, or
batch number, or
any other suitable identification data.

26. The system of claim 21, further comprising reagents necessary for conducting a diagnostic assay selected from the group consisting of reaction buffers, enzymes, primers, probes, nucleotides and combinations thereof.

27. The system of claim 21, wherein the reaction vessel further comprises a label including visual indicia identifying the reaction vessel.

28. The system of claim 27, wherein the label includes a removable portion.

29. The system of claim 28, wherein the removable portion includes at least a written representation of the reaction vessel identity.

30. The system of claim 21, wherein the thermal cycler comprises a single-button user interface.

31. A method of operating a thermal cycler comprising:
1) a remote tag reader;
2) a computer readable medium that contains data associating one or more reaction vessel identities with specific operations to be performed on a corresponding identified reaction vessel; and
3) a computer that reads the computer readable medium, the method comprising:
 i) providing a reaction vessel including an identification tag readable by the remote tag reader, wherein the identification tag includes data identifying the reaction vessel;
 ii) placing the reaction vessel in sufficient proximity to the thermal cycler so that the readable identification tag can be read by the remote tag reader;
 iii) operating the thermal cycler so that it:
  reads the readable identification tag to determine the identity of the reaction vessel;
  queries the computer readable medium with the determined identity so that the associated specific operations for the determined identity are selected;
  performs the selected specific operations on the identified reaction vessel; and
  displays one or more results of the performed specific operations.

32. The method of claim 2, wherein the radio tag is an RFID tag.

33. The system of claim 22, wherein the radio tag is an RFID tag.

34. The system of claim 29, wherein the removable portion further comprises an area on which a user may write additional information.

35. The system of claim 21, wherein the thermal cycler further comprises a display.

* * * * *